(12) United States Patent
Orikasa

(10) Patent No.: US 6,843,651 B2
(45) Date of Patent: Jan. 18, 2005

(54) ORTHODONTIC BRACKET

(75) Inventor: Masaaki Orikasa, Futaba-gun (JP)

(73) Assignee: Tomy Incorporated, Fukushima (JP)

( * ) Notice: Subject to any disclaimer, the term of this patent is extended or adjusted under 35 U.S.C. 154(b) by 233 days.

(21) Appl. No.: 10/084,203

(22) Filed: Feb. 28, 2002

(65) Prior Publication Data
US 2002/0119414 A1 Aug. 29, 2002

(30) Foreign Application Priority Data

Feb. 28, 2001 (JP) ..................................... P.2001-055644

(51) Int. Cl.$^7$ ............................................. A61C 3/00
(52) U.S. Cl. ............................................. 433/13; 433/9
(58) Field of Search ................................. 433/9, 10, 11, 433/13, 19, 14

(56) References Cited

U.S. PATENT DOCUMENTS

| 3,772,787 A | * 11/1973 | Hanson | 433/14 |
| 4,248,588 A | * 2/1981 | Hanson | 433/11 |
| 4,492,573 A | * 1/1985 | Hanson | 433/11 |
| 4,712,999 A | * 12/1987 | Rosenberg | 433/8 |
| 5,474,445 A | 12/1995 | Voudouris | |
| 5,562,444 A | * 10/1996 | Heiser et al. | 433/11 |
| 5,586,882 A | * 12/1996 | Hanson | 433/13 |
| 5,630,715 A | * 5/1997 | Voudouris | 433/8 |
| 5,685,711 A | 11/1997 | Hanson | |
| 5,906,486 A | 5/1999 | Hanson | |
| 5,911,574 A | 6/1999 | Casey | |
| 6,071,119 A | 6/2000 | Christoff et al. | |
| 6,071,120 A | 6/2000 | Birkel | |
| 6,142,775 A | 11/2000 | Hansen et al. | |
| 6,168,428 B1 | 1/2001 | Voudouris | |
| 6,368,105 B1 | * 4/2002 | Voudouris et al. | 433/11 |

FOREIGN PATENT DOCUMENTS

| DE | 198 56 794 A1 | 6/2000 |
| EP | 1 090 604 A2 | 4/2001 |
| WO | 02/07637 A1 | 1/2002 |

* cited by examiner

Primary Examiner—Ralph A. Lewis
(74) Attorney, Agent, or Firm—Sughrue Mion, PLLC

(57) ABSTRACT

An orthodontic bracket enabling to securely maintain positive pressure of an archwire effecting to the bottom of an archwire slot even if doing the rotational control more than a determined amount. The orthodontic bracket has a base, a main body furnished on the base, an archwire slot formed in the main body, a guiding part crossing with the slot, and a band-like clip guided in the guiding part. A clip is curved in U-shape as covering at least one part of a reverse base side in the archwire slot, and a locking portion furnished at one end side in the length direction of the clip creeps under a cover portion supported by the main body. The locking claw formed in the locking portion and a covering claw formed in the cover portion get over and engage each other.

18 Claims, 14 Drawing Sheets

ORTHODONTIC BRACKET

BACKGROUND OF THE INVENTION

The present invention relates to an orthodontic bracket, and in particular such an orthodontic bracket enabling to secure positive pressure effecting to an archwire received in an archwire slot for correcting irregularities of the teeth, and enabling to maintain the pressure for a long time.

FIG. 14A shows an orthodontic bracket 100 correcting a row of teeth. The orthodontic bracket 100 comprises a mask-like base 101 attached to a enamel surface of tooth, a bracket main body 102 furnished on the base 101 at its one side, an archwire slot 103 formed in the bracket main body 102, a guiding part 104 formed at the base side 101 and penetrating in a transverse direction with the archwire slot 103, and a band-like clip 105 guided in the guiding part 104 (hereinafter defined as a prior art example 1).

With respect to the orthodontic bracket 100, the clip 105 is curved in substantial U-shape as covering at least one part of a side (the upper part in FIG. 14A) opposite to the base 101 in the archwire slot 103, holding portions 106, 106 furnished at one end sides in the length direction of the clip 105 are engaged as creeping under cover portions 107, 107 furnished in the bracket main body 102, thereby to press down an archwire (not shown) toward a bottom of the archwire slot 103.

Depending on this orthodontic bracket 100, in comparison with conventional orthodontic brackets, rotational control and torque control of the archwire for correcting irregularities of the teeth or rotated teeth may be improved.

Further, such an orthodontic bracket 100 obtains excellent effects that can solve following problems (i) to (iii) that are occurred when a ligature wire (not shown) is employed.
  (i) complication of ligating work;
  (ii) complicating treatment of cut-off ends of the ligature wire; and
  (iii) reduction of aesthetic appreciation.

Furthermore, the orthodontic bracket 100 also obtains excellent effects that can solve following problems (i) to (ii) that are occurred when an elastomeric ligature ring is (not shown) is employed.
  (i) reduction of ligating force on the archwire owing to its permanent elongation; and
  (ii) discoloration by foods and drinks resulting poor aesthetic appreciation.

Moreover, the orthodontic bracket 100 further obtains excellent effect that can solve hygienic problems by food debris as problems occurring in common when employing the ligature wire or the elastomeric ligature ring. Incidentally, since the above mentioned prior art example 1 makes engagement, as shown in FIG. 14B, by causing the holding portions 106 of the clip 105 to creep under the cover portions 107, if making the rotational control more than a determined amount, the archwire 108 pushes up the clip 105, whereby the holding portion 106 of the clip 105 probably gets out from the cover portion 107 of the bracket main body 102. This problem similarly happens when using a square and rectangular wire near a full size.

On the other hand, the orthodontic bracket 200 shown in FIG. 15A has a groove 210 transverse with the archwire slot 203 of the bracket main body 202 supported by the base 201, and at the same time it has a fitting member 220 made of elastomer or resin having flexibility (U.S. Pat. No. 6,142,775, hereinafter referring a prior art example 2).

This prior art example 2 has bar-like anchoring parts 221, 222 at both ends in the length direction of the fitting member 220, and the anchoring part 222 is engaged with tie-wing parts 209, 209 at an occlusal side of the bracket main body 202, and then if the locking part 221 is engaged with tie-wing parts 208, 208 at a gingival side of the bracket main body, the fitting member presses down the archwire slot.

In addition, the prior art example 2 sets forth that a pair of arms 223, 223 project from a spine of the fitting member 220 as illustrated in FIG. 15B, and if these arms 223, 223 are fitted in the archwire slot 203, the rotational control is made possible.

However, in the prior art example 2, since the fitting member 220 made of elastomer or resin having flexibility presses down into the groove 210 crossing with the archwire slot 203, this embodiment is similar to the case of ligation with the elastomeric ligature ring, and enough effect might be probably little available.

Further, with respect to the prior art example 2, even if the pair of arms 223, 223 projecting from the fitting member 220 are fitted in the archwire slot 203, since each arm 223 has almost equal width and size to those of the archwire slot 203 and is made of elastomer or resin having flexibility, the rotational control might not be effective.

The prior art example 2 is difficult to be handled because of the shape or small size and causes troublesome works to doctors. In addition, the prior art example 2 has a risk of the fitting member 220 getting out from the bracket main body 202 by taking meals or brushing thereafter.

Besides, in the prior art example 2, since the fitting member 220 elastically presses down the archwire 211, a problem occurs that a friction free state is not provided which is required to a fine archwire used at an initial stage.

SUMMARY OF THE INVENTION

The invention has been realized in view of the above mentioned problems, and it is an object of the invention to provide an orthodontic bracket enabling to securely maintain positive pressure of the archwire effecting to the bottom of the archwire slot even if doing the rotational control more than a determined amount.

The above-mentioned object can be achieved by an orthodontic bracket according to the present invention that comprises a base, a bracket main body, a guiding part, a cover portion and a band-shaped clip. The base is to be attached to a tooth enamel surface. The bracket main body is formed on the base and includes a groove-shaped archwire slot with an opening that is opened in a direction opposite to the base. The guiding part is formed in at least one of the bracket main body and the base. The guiding part crosses the archwire slot. The cover portion is supported by the bracket main body and has a covering claw. The band-shaped clip is guided by the guiding part and is curved in substantially U-shape in its cross section when the clip is attached to the bracket main body. The clip has a holding part that covers at least a portion of the opening of the archwire slot. The clip has a locking portion that is formed at one end of the clip in its longitudinal direction. The locking portion has a locking claw. In the present invention, the locking claw and the covering claw are brought in engagement with each other at a mutual locking position.

In the above-mentioned orthodontic bracket, it is preferable that the locking claw and the covering claw are brought in engagement with each other at the mutual locking position when the archwire slot receives therein an archwire having a cross-sectional size more than a predetermined size.

In the above-mentioned orthodontic bracket, the holding part of the clip may press the archwire toward the bottom side of the groove-shaped archwire slot.

In addition, in the orthodontic bracket it is advantageous that the locking claw and the covering claw are positioned to be engageable each other when said archwire slot receives therein an archwire having a cross-sectional size less than the predetermined size.

Further, in the orthodontic bracket it is advantageous that the locking claw and the covering claw are slidably brought in contact with each other when the clip is assembled with the bracket main body, thereby enabling to maintain a condition where the locking claw and the covering claw engage each other.

Furthermore, in the orthodontic bracket it is advantageous that the covering claw is deformable by a determined angle around a fulcrum of the cover portion in such a manner that the covering claw is slidably engaged and locked into place by the locking claw.

Moreover, in the orthodontic bracket it is advantageous that the cover portion is integrally formed with the main body, and the clip has a restriction part that is formed at the other end of the clip in its longitudinal direction and positions the clip relative to the main body.

In the orthodontic bracket, it is preferable that the cover portion is integrally formed with the clip.

In addition, in the orthodontic bracket, it is preferable that the covering claw is deformable by a determined angle around a fulcrum of the cover portion for releasing the engagement between the covering claw and the locking claw disengaging the covering claw and the locking claw.

Further, in the orthodontic bracket it is more preferable that the cover portion comprises:

a lever for receiving external force so as to deform the covering claw.

Furthermore, in the orthodontic bracket, it is preferable that the lever comprises a concave portion that is adapted to receive a predetermined releasing instrument.

In the orthodontic bracket according to the present invention, it is advantageous that at least one of the locking claw and the covering claw has a tapered step portion.

In the orthodontic bracket according to the present invention, it is advantageous that the holding part of the clip has a larger width as compared with remaining part.

In the orthodontic bracket according to the present invention, it is advantageous that the clip has a drawing hole that is adapted to receive a releasing instrument for releasing an engagement between the covering claw and the locking claw.

In the orthodontic bracket according to the present invention, it is advantageous that the holding part of the clip has an arc-shaped cross sectional shape along its width direction, thereby pressing down the archwire towards the bottom of the archwire slot while the clip is being elastically deformed so that the cross sectional shape is to be flat.

The above-object can also be achieved by, according to one aspect of the present invention, an orthodontic bracket that has a mask-like base, a bracket main body, a groove-like archwire slot, a guiding part, and a band-like clip. The mask-like base is attached to the tooth enamel surface. The bracket main body is furnished on the base at its one side. The groove-like archwire slot is formed in the bracket main body. The guiding part is formed in at least one of the bracket main body and the base and continuous in a transverse direction with the archwire slot. The band-like clip-is guided in the guiding part. The clip is curved almost in U-shape as covering at least one part of a reverse base side in the archwire slot. A locking portion furnished at one end side in the length direction of the clip is engaged as creeping under a cover portion supported by the bracket main body.

Herein, as the guiding part, there are exemplified a guiding part formed between the base and the archwire slot, or a groove formed in the attached face of the base.

In case the groove is formed as the guiding part in the attached face of the base, it is sufficient to receive the clip in the groove, followed by closing the groove with a determined material to form a continuous face.

For accomplishing the object, in an aspect (1) of the invention, a locking claw is provided at the locking portion, and a covering claw is provided at the cover portion. The locking claw and the covering claw pass each other at a mutual locking position, so that the clip closes the archwire slot at one end side thereof in the length direction.

Herein, with respect to the locking claw and the covering claw, as an aspect (2) of the invention, the clip solely may press down the archwire slot at one end side in the length direction, irrespective of the locking condition between the locking claw and the covering claw.

Therefore, in such an orthodontic bracket, the friction free state is provided which is required to a fine archwire used at a initial stage, and the pressure of the archwire can be maintained securely and positively to a comparatively thick archwire during second and final stages.

Further, with respect to the locking claw and the covering claw, as an aspect (3) of the invention, if the locking claw and covering claw are disposed at positions enabling to relatively engage each other, when strong rotational control occurs, the clip is upheaved at one end for engaging the locking claw and the covering claw.

Therefore, in the orthodontic bracket, when strong rotational control occurs, the locking claw and the covering claw are engaged, so that the clip can be avoided from getting out of the bracket main body.

Still further, with respect to the locking claw and the covering claw, as an aspect (4) of the invention, if the locking claw and the covering claw elastically get over each other, thereby enabling to maintain a condition where the locking claw and the covering claw engage each other, the engagement of the locking claw and the covering claw can be securely maintained, irrespective of thickness of the archwire, so that the clip can be avoided from getting out of the bracket main body.

Herein, if the locking claw and the covering claw are shaped in claw of taper in cross section, both get over as elastically sliding the slant faces and passing each other.

With respect to the locking claw and the covering claw, as an aspect (5) of the invention, in case the locking claw and the covering claw elastically get over each other, so that the covering claw is turnable till a determined angle around a fulcrum of the base of the cover portion under the condition where the locking claw and the covering claw engage each other, even if strong rotational control is created as the covering claw is turned and deformed via the locking claw, part of force holding the archwire is received by elasticity of the cover portion, and at the same time the clip and the cover portion cooperate to press down the archwire.

In the above mentioned orthodontic bracket, under the friction free state which is required to the archwire used at an initial stage or even when requiring the heavy rotational control for malposed teeth or crowded teeth, and under the positive pressure of the comparatively thick archwire used after the middle term of the curing. It is possible to avoid possibility that the locking portion of the clip gets out from the cover portion of the bracket main body as happening in prior arts depending on circumstances, whereby the object of the invention can be accomplished.

As an aspect (6) of the invention, as the cover portion is unified with the bracket main body, while a restriction part is provided at the other end in the length direction of the clip, the force pressing down the archwire toward the bottom of the archwire slot can be borne by deforming load of the cover portion other than the clip.

Also when the clip is slid by positioning the clip to open the archwire slot, the clip can be avoided by restriction part from getting out of the bracket main body.

On the other hand, as an aspect (7) of the invention, as the cover portion is unified with the clip in the length direction thereof, the clip and the cover portion may be made of soft materials having flexibility, and the bracket main body may be made of hard materials.

For the orthodontic bracket, a plurality of kinds of bracket main bodies and clips different in specifications, dimensions and others are prepared in advance, and if associating them appropriately, variations can be easily broadened.

As an aspect (8) of the invention, since the cover portion turns over a determined angle around a fulcrum of a base of the cover portion for releasing the covering claw from the locking claw, thereby enabling to release the mutual engagement of the locking portion and the cover portion, the clip is slid in a tooth-axial direction to open the archwire slot, and the archwire can be easily removed from the archwire slot.

That is, in this orthodontic bracket, the archwire can be securely held and easily exchanged, so that the exchanging work can be rapidly carried out, thereby enabling to lighten burden on a patient and an orthodontist.

As an aspect (9) of the invention, as a lever is furnished in the cover portion for receiving external force tilting the cover portion, if the operator hooks the lever at his fingers, nails or a tip-end of an instrument, the locking portion and the cover portion can be engaged or released securely and easily.

As an aspect (10) of the invention, as the lever is formed with a concave for receiving a suitable instrument, if the operator hooks the lever at his fingers, nails or the tip-end of the instrument, the locking portion and the cover portion can be engaged or released more securely and easily.

An aspect (11) of the invention is, as set forth in the aspects (4) and (5), characterized in that at least one of the locking claw and the covering claw has a slant face directing to the other, the face being shaped in taper in cross section, and the one is arranged with saw edges in cross section of one step or more perpendicular to a tooth axial direction.

Herein, either one of the locking claw and the covering claw may have the saw edge in cross section, otherwise both may have respectively the saw edges.

In the thus composed orthodontic bracket, at least one of the locking claw and the covering claw may have the saw edge in cross section perpendicular to the tooth-axial direction, so that the locking claw and the covering claw elastically and easily get over each other.

If this orthodontic bracket has a plurality of one or both of the locking claw and the covering claw, the pressure of the archwire may be adjusted to the archwire slot by appropriately selecting the relative position of the locking portion and the cover portion.

As an aspect (12) of the invention, preferably the base and the bracket main body have light permeability, and as an aspect (13) of the same, preferably the base and the bracket main body are filler containing resins, and the filler increases durability of the base and the bracket main body and brings out a tint of white and semi-transparency.

It is desirable that as an aspect (14) of the invention, the clip has the light permeability, as an aspect (15), the clip is made of resin, and as an aspect (16), more desirably the clip is a filler containing resin, and the filler increases durability of the clip and brings out a tint of white and semi-transparence.

Herein, the light permeability means to include a case that the base, the bracket main body and the clip are made of non-colored resin, another case that, e.g., a blank material itself is semi-transparent or transparent as ceramics or glass, or a further case that resins, ceramic or glass are colored by containing pigments or dyes in predetermined material quality. When coloring the base, the bracket main body or the clip, it is desirable to make colors similar to the colors of the teeth.

In the thus composed orthodontic bracket, as the base, the bracket main body and the clip have the light permeability, an excellent aesthetic appreciation may be effected in comparison with non-light permeability.

As the clip, materials having flexibility curving in U-shape may be exemplified such as polyurethane, polypropylene, polyethylene, PET, polyamide, polycarbonate, polyethersulfone, polyallylate, or polyphenylenesulfide.

As the orthodontic bracket has the clip made of resin, complicated shapes can be easily obtained in comparison with the metal-made clip, and as the blank material itself has elasticity over a very broad range, the pressure of the archwire may be obtained to the archwire slot.

In case the base, the bracket main body and the clip are formed with the filler contained resin, it is sufficient to employ such fillers as glass fiber or glass beads increasing durability and drawing hue of white and semi-transparence.

In an aspect (17) of the invention, a holding part may be extended from the determined position of the clip in the width direction, and the clip and the holding part can press down the archwire from the reverse side of the base of the archwire slot.

Herein, the whole area of the reverse base designates generally a labial side (lip side), and the case of a lingual bracket designates a lingual side (tongue side). The holding part may have a width in a mesiodistal direction equal to the mesiodistal size of the bracket main body, or may extend beyond the width of the mesiodistal direction of the bracket.

The holding part may cooperate with the clip for pressing down the archwire, and it may be sole to pressing down the archwire, irrespective of presence or absence of the pressure relative to the archwire caused by the clip.

In such an orthodontic bracket, as the holding part extending from the clip may press the archwire from the reverse side of the archwire slot, the rotational control can be exactly carried out to the archwire.

As an aspect (18) of the invention, the drawing hole is formed for receiving an appropriate instrument at a determined position in the clip under a condition where the locking portion and the cover portion are engaged each other, and therefore after the mutual engagement of the locking portion and cover portion is released, an operator hooks the tip-end of the instrument into the drawing hole, thereby easily drawing out the locking portion from the cover portion.

As an aspect (19) of the invention, a cross sectional shape of the clip is almost arc along the width direction at a place pressing down the archwire, and presses down the archwire while the clip is being elastically deformed so that the cross sectional shape is to be flat, the pressure of the archwire to the archwire slot is made available owing the elastic resiliency of the place recovering to an initial shape.

DETAILED DESCRIPTION OF THE PREFERRED EMBODIMENTS

The embodiments according to the invention will be explained referring to the attached drawings. In each of the embodiments, a twin bracket is exemplified as the orthodontic bracket, but the invention is applicable to a single bracket, and is not limited to the twin bracket.

Figure 1:
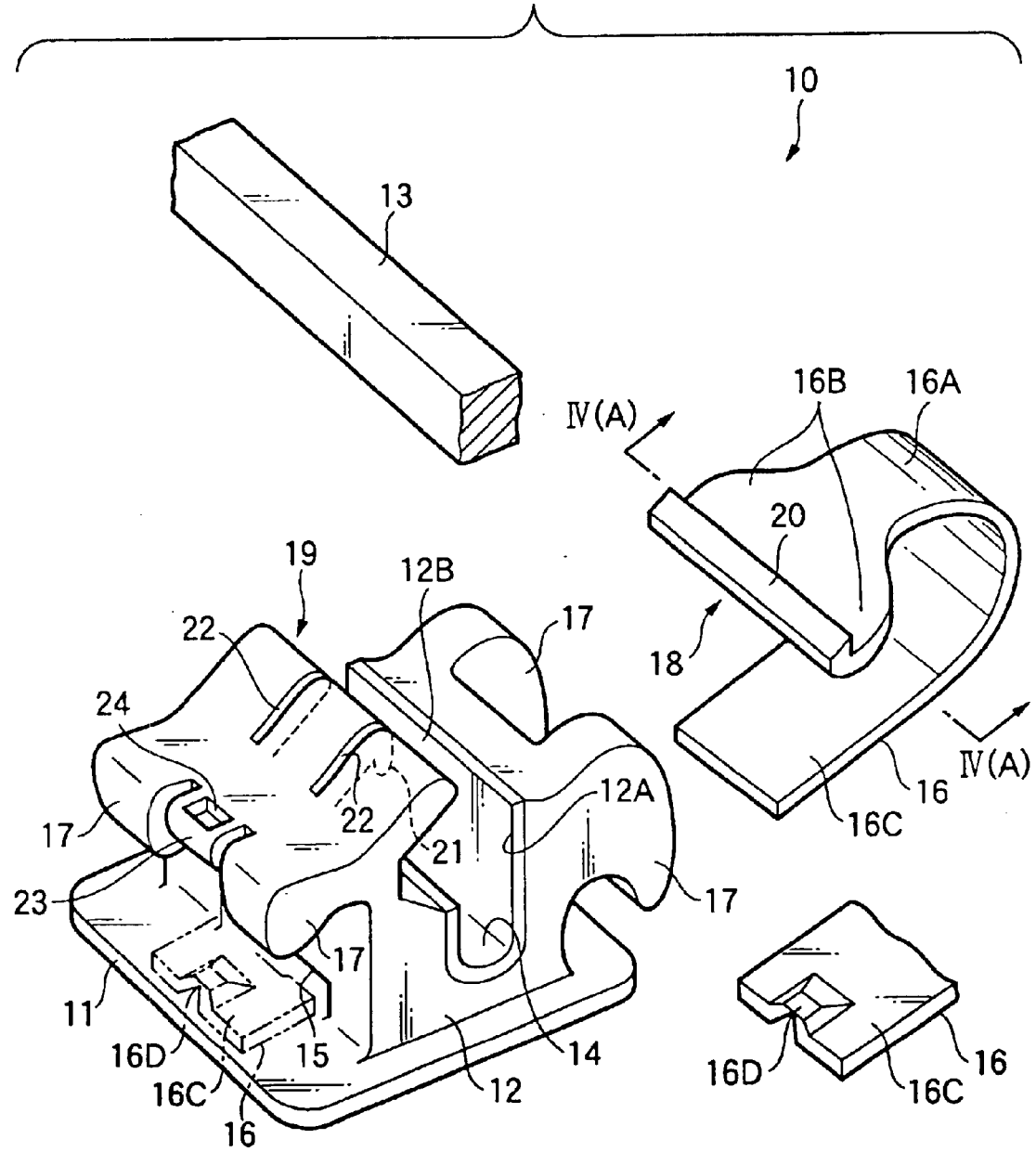
FIG. 1 is a whole perspective view showing the first embodiment according to the invention.

As seeing in FIG. 1, the orthodontic bracket 10 of a first embodiment according to a first aspect of the present invention is the twin bracket comprises, a mask-like base 11 attached to the enamel surface of a tooth, a bracket main body 12 furnished on the base 11 at its one side, a groove-like archwire slot 14 formed in the bracket main body 12 and rectangular in cross section for receiving the archwire 13, a guiding part 15 formed between the base 11 in the bracket main body 12 and an archwire slot 14, a band-like clip 16 guided in the guiding part 15, and four tie-wings 17 provided outside of the bracket main body 12.

The base 11 has a concaved spherical face corresponding to the tooth enamel surface and is to bond to the tooth enamel surface.

The bracket main body 12 is a block having a groove 12A continuous in a transverse direction with respect to the bracket main body and is formed with an archwire slot 14 by inserting a metal liner 12B of U shape in cross section into the groove 12A. The metal liner 12B has an inside shape and an inside dimension corresponding to the cross sectional shape and dimension of the archwire 13.

The base 11 and the bracket main body 12 are made of appropriate resin, glass or ceramics having rigidity and bondability.

Herein, in case the base 11 and the bracket main body 12 are ceramic, a blank material is semi-transparent in itself. Being resin or glass, the base 11 and the bracket main body 12 have hues similar the teeth and are colored to be semi-transparent by containing pigments or dyes in determined material qualities.

Further, in case the base 11 and the bracket main body 12 are resin, the resin contains the filler mixed with e.g., glass fiber or glass beads, and the filler increases durability of the base 11 and the bracket main body 12, and brings out a tint of white and semi-transparence.

The guiding part 15 is formed as a penetrating hole crossing with a predetermined angle with respect to the continuous direction of the archwire slot 14.

The clip 16 is made of a resin having flexibility curving in U-shape and high elasticity such as polyurethane, polypropylene, polyethylene, PET, polyamide, polycarbonate, polyethersulfone, polyallylate, or polyphenylenesulfide, and is determined to be 0.3 to 0.8 mm in thickness. The clip 16 is colored to be semi-transparent similarly to the teeth by containing non-color, pigment or dyes, and has the light permeability.

Further, the clip 16 is a filler containing resin mixed with glass fiber or glass beads, and the filler increases durability of the clip 16 and brings out a tint of white and semi-transparence.

The clip 16 enlarges a width size as expanding one end side 16A in the length direction (upper side in FIG. 1) from a determined position toward the end part, and is formed with a pair of large width parts 16B, 16B extending from both ends of the clip 16.

Therefore, the clip 16 is curved almost in U-shape under a condition that the other end side 16C in the length direction (lower side in FIG. 1) is lead into the guiding part 15, and then when the clip 16 moves in parallel, and the locking portion 18 formed in the one end side 16A in the length direction engages as creeping under the cover portion 19 supported by the bracket main body, the clip 16 and the large width parts 16B, 16B cover all over the reverse base side of the archwire slot 14.

By the way, the archwire slot 14 in the orthodontic bracket 10 opens toward the labial side (lip side), but in the case of the lingual bracket, the archwire slot 14 opens toward the lingual side (tongue side).

The other end side 16C in the length direction (lower side in FIG. 1) is inserted in the guiding part 15, and then the clip 16 is positioned by a restriction portion 16D formed by an appropriate thermal process in the other end side 16C in the length direction, so that the clip 16 cannot be withdrawn.

Figure 2A:
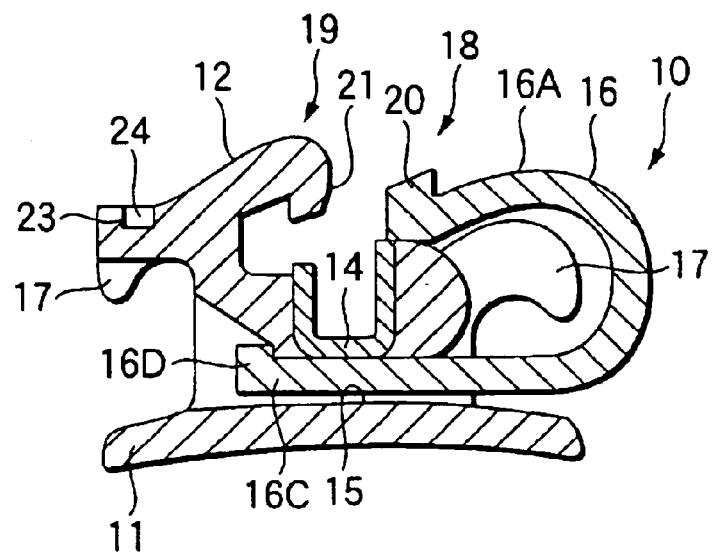
FIGS. 2(A) and 2(B) are a cross sectional view and a plan view showing the orthodontic bracket of the first embodiment.
Figure 2B:
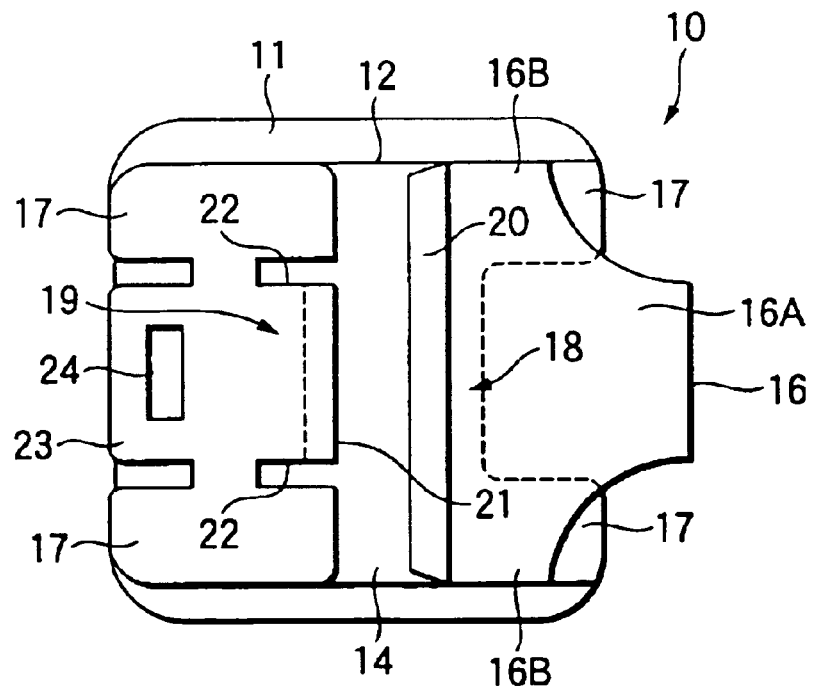
Figure 3A:
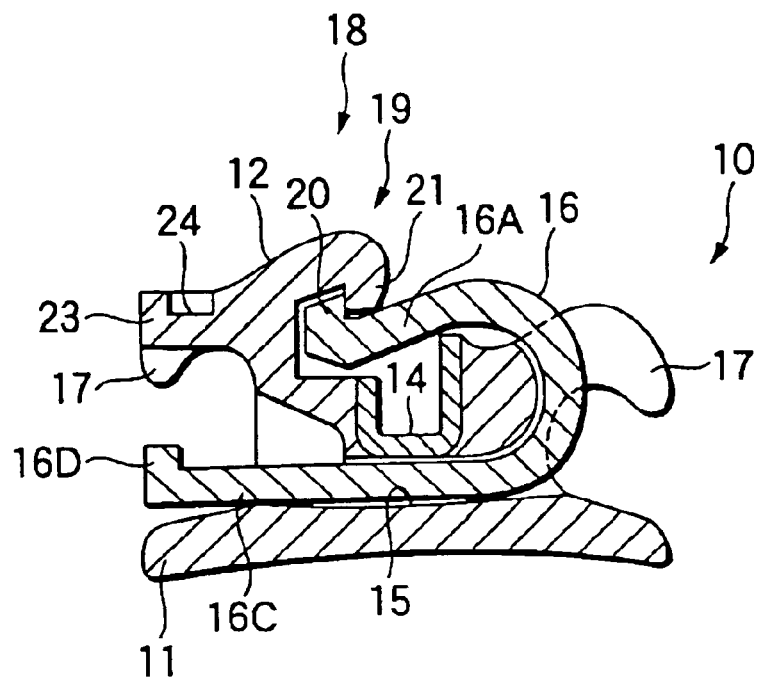
FIGS. 3(A) and 3(B) are a cross sectional view and a plan view showing the orthodontic bracket of the first embodiment.
Figure 3B:
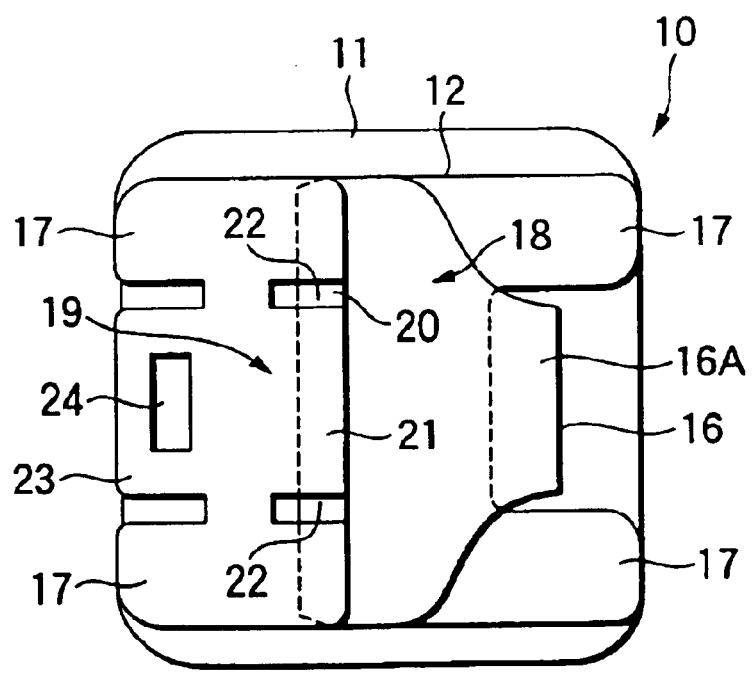

As illustrated in FIGS. 2 and 3, the present orthodontic bracket 10 is based on the invention having the locking claw 20 formed in locking portion 18 and the covering claw 21 formed in the cover portion 19.

The locking claw 20 has a slant face directing to one end in the length direction of the clip 16, the face being shaped in taper in cross section, and the cross sectional shape thereof continues along the edge of one end 16A in the length direction of the clip 16.

On the other hand, the covering claw 21 is integrally formed along the edges between a pair of slits 22, 22 (see FIG. 1), tapering from the cover portion 19 toward clip 16.

When the locking portion 18 creeps under the cover portion 19, the locking portion 18 and the cover portion 19 get over each other as the locking claw 20 and the covering claw 21 are elastically sliding the respective slopes, and in company with this movement in a manner as the covering claw 21 separates from the locking claw 20, the cover portion 19 turns around the fulcrum of the base thereof and deforms, and then the cover portion 19 recovers to the initial condition, whereby the locking claw 20 and the covering claw 21 are brought in engagement with each other.

The locking portion 18 and the cover portion 19 maintain the engagement of the locking claw 20 and the covering claw 21.

Figure 4A:
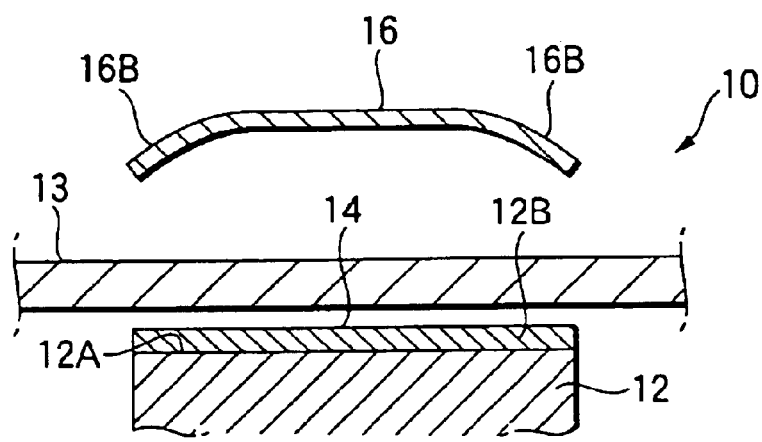
FIGS. 4(A) to 4(D) are cross sectional views showing the archwire slot.
Figure 4B:
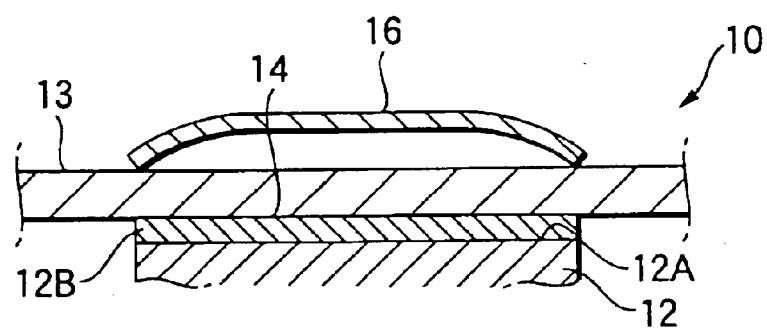

At this time, as illustrated in FIG. 4A, the cross sectional shape following the width direction of the places formed with the large width parts 16B, 16B in the clip 16, is arc in recess corresponding to the bottom of the archwire slot 14, and as illustrated in FIG. 4B, the clip 16 is contacted to the archwire 13 while deforming the clip 16 as the cross sectional shape becomes flat, so that elastic resiliency exerts to recover the cross sectional shape to the initial shape, whereby the archwire 13 can be favorably pressed toward the bottom of the archwire slot 14.

Figure 4C:
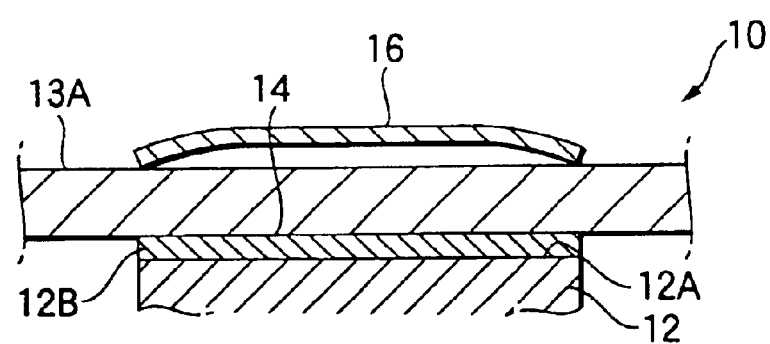

The orthodontic bracket 10 is shaped in recess arc in cross section at the determined position of the clip 16, and as illustrated in FIG. 4C, even when using an archwire 13A of larger diameter than the archwire 13 or a square and rectangular wire (not shown) near a full size, a deforming degree of the clip 16 at said cross sectional shape becomes large, whereby a correspondence is available.

Figure 4D:
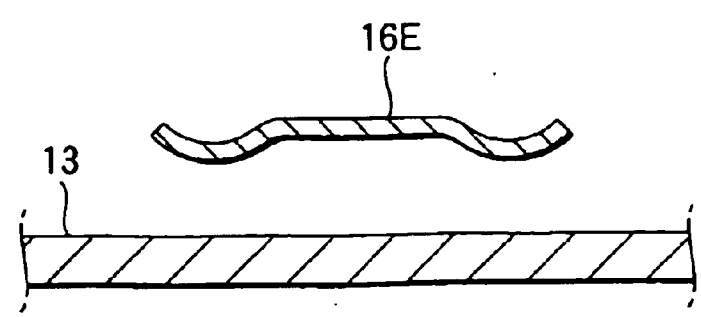

The cross sectional shape in the determined position of the clip 16 is not always shaped in recess arc for the bottom of the archwire slot 14, and as illustrated in FIG. 4D, it may be shaped with a pair of convex arcs for the bottom of the archwire slot 14.

Depending on such a clip 16E, both edges in width of the clip 16 are caught at the circumference of the archwire 13, so that an effect is brought about not to hinder the friction free state which is required to the fine archwire used at the initial stage.

In the above mentioned orthodontic bracket, for taking out the archwire 13 from the archwire slot 14, the operator turns to deform the cover portion 19 around the fulcrum of its base portion for releasing the mutual engagement between the locking portion 18 and the cover portion 19 in such a manner that the covering claw 21 separates from the locking claw 20 via the lever 23 extending in the direction remote from the cover portion 19.

At this time, if the operator engages with the recess 24 formed in the lever 23 at the tip-end of the determined instrument, the cover portion 19 is easily deformed.

Then, the clip 16 moves in parallel to release the archwire slot 14 for taking out the archwire 13.

Depending on the orthodontic bracket 10, the locking claw 20 of the locking portion 18 and the covering claw 21 of the cover portion 19 elastically get over and pass each other, so that one side in the length direction of the clip 16 is possible to maintain the archwire slot 14 pressed down, and therefore, if doing the rotational control over a certain limit, it is possible to exactly maintain the archwire 13 positively pressing down toward the bottom of the archwire slot 14.

In particular, the orthodontic bracket 10 may keep the locking claw 20 and the covering claw 21 engaged each other, so that a desired effect may be brought about when a strong rotational control is required for malposed teeth or rotated teeth.

When the strong rotational control is loaded, the locking claw 20 and the covering claw 21 are met as much, the clip 16 is urged upward, and two members do not get out.

Further, in this orthodontic bracket 10, the cover portion 19 is integrally unified with the bracket main body 12 and a restriction portion 16D is formed in the other side 16C in the length direction of the clip 16, and so even when the clip 16 slides and releases the archwire slot 14, the clip 16 is avoided from getting out of the bracket main body 12.

Following the orthodontic bracket 10, the cover portion 19 is turned around the fulcrum of its base portion in such a manner that the covering claw 21 separates from the locking claw 20 for releasing the mutual engagement between the locking portion 18 and the cover portion 19, and the archwire 13 can be easily taken out from the archwire slot 14, so that the exchanging work can be rapidly carried out, thereby enabling to lighten burden on the patient and the operator.

The cover portion 19 is especially formed with the lever 23 for receiving the external force as deforming the cover portion 19, and if the operator hooks this lever 23 at his fingers, nails or the tip-end of the instrument, the locking portion and the cover portion can be released more securely and easily from the mutual engagement.

Besides, as the lever 23 is formed with the concave 24 for receiving an appropriate instrument, if the operator hooks the lever at his fingers or the tip-end of the instrument, the locking portion and the cover portion can be engaged or released more securely and easily.

Based on the orthodontic bracket 10, as the base 11, the bracket main body 12 and the clip 16 have the light permeability, an excellent aesthetic appreciation may be effected in comparison with non-light permeability.

As the orthodontic bracket 10 has the clip 16 made of resin, complicated shapes can be easily obtained in comparison with the metal-made clip, and as the blank material itself has elasticity over a very broad range, the pressure of the archwire 13 may be obtained to the archwire slot 14.

In this orthodontic bracket 10, the large width parts 16B, 16B extending from the determined positions of the clip 16 in the width direction are possible to cover allover the labial side (lip side) of the archwire slot 14, and so the rotational control of the archwire 13 can be exactly undertaken.

In particular, the clip 16 is almost arc in cross section in the width direction at the part of pressing down the archwire slot 14 to be flat as being elastically deformed, so that the pressure is effected to the archwire 13 in the transverse ends than the width of the clip 16.

FIGS. 5 to 9 show the orthodontic bracket 50 of a second embodiment according to the invention. In the second embodiment explained in the following description, as to the members already explained in FIGS. 1 to 4, explanation will be briefed or omitted by applying the same or corresponding signs in the drawings.

Figure 5:
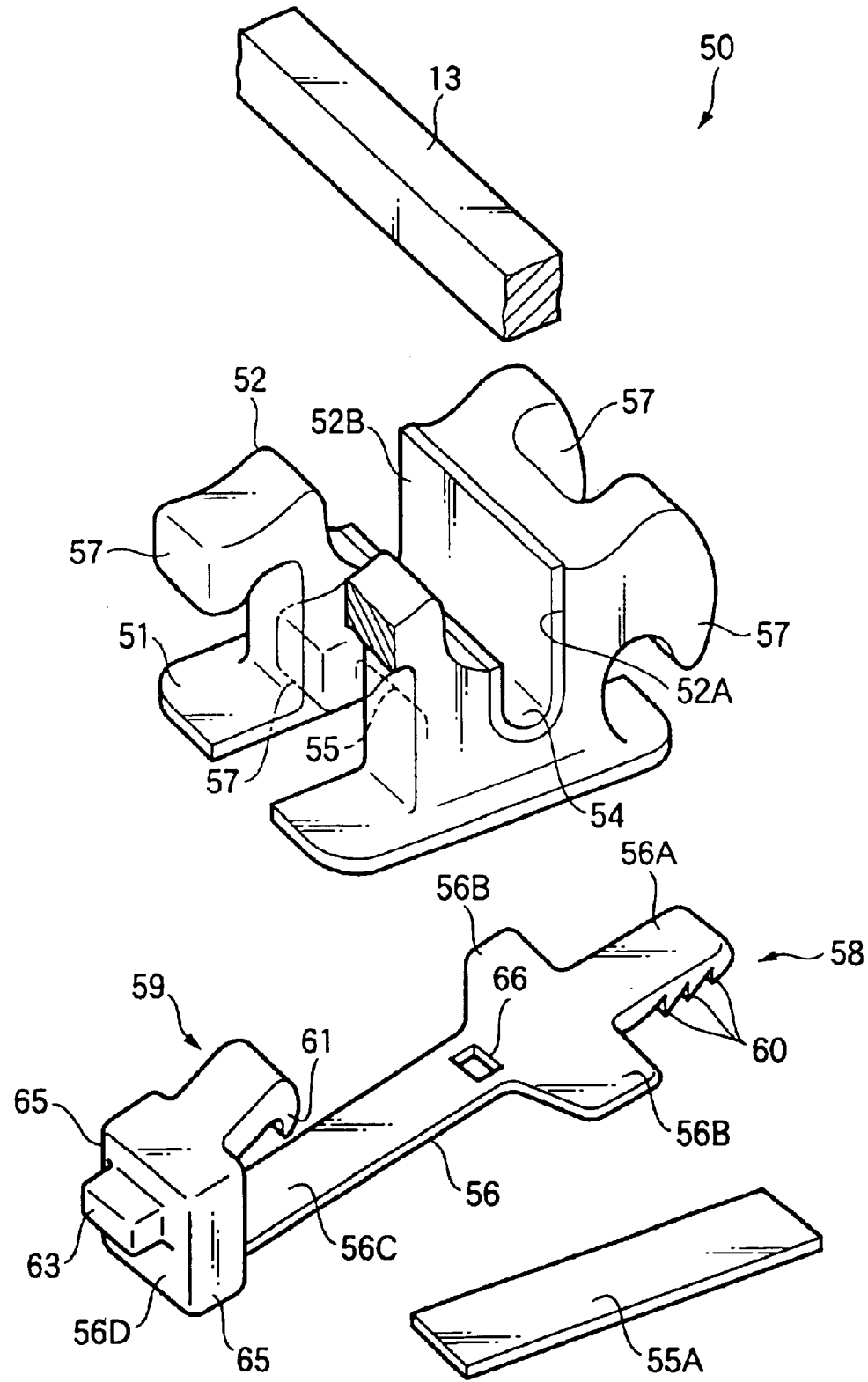
FIG. 5 is a whole perspective view showing the second embodiment according to the invention.
Figure 6:
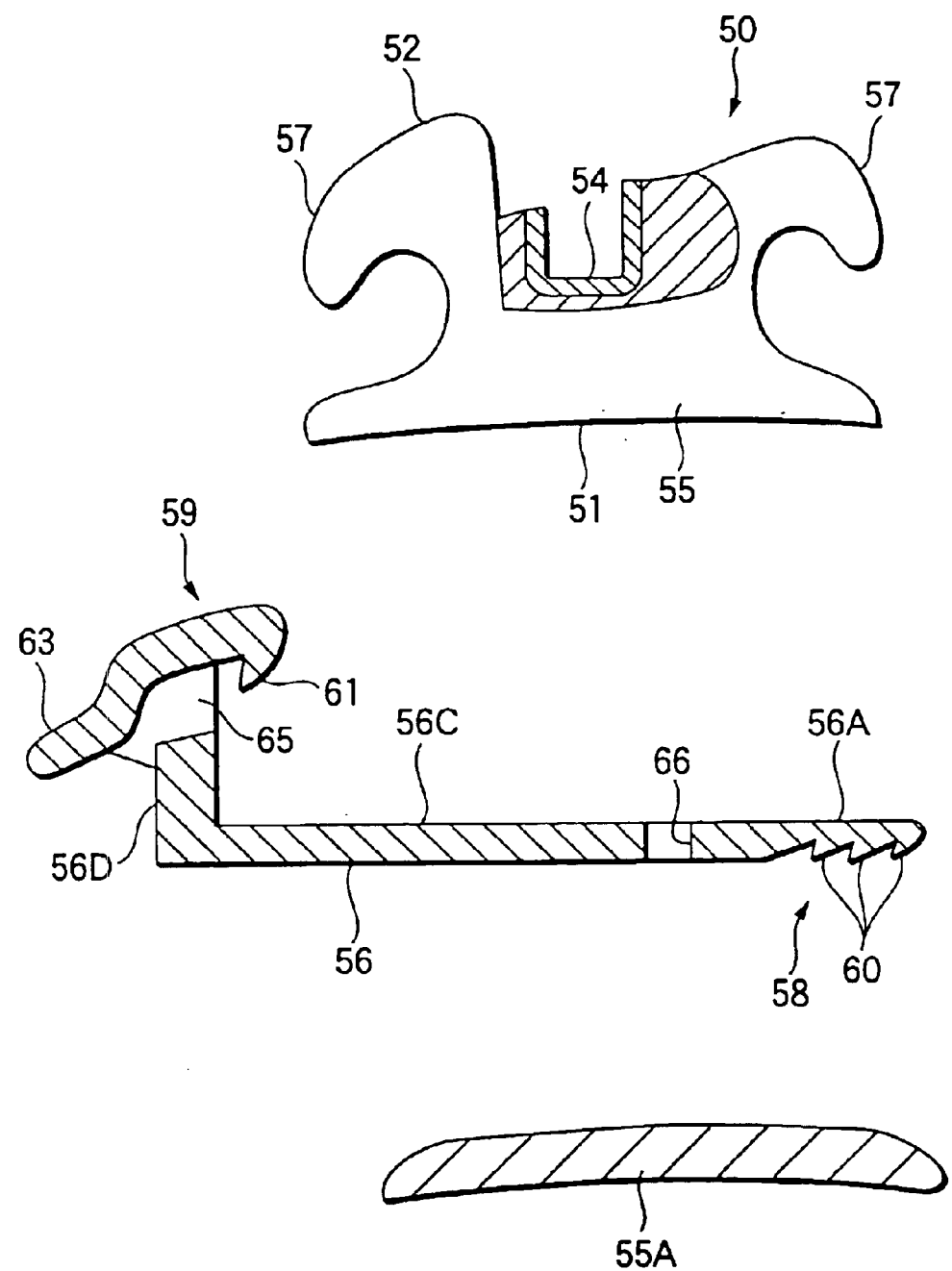
FIG. 6 is a cross sectional view showing the orthodontic bracket of the second embodiment.
Figure 7:
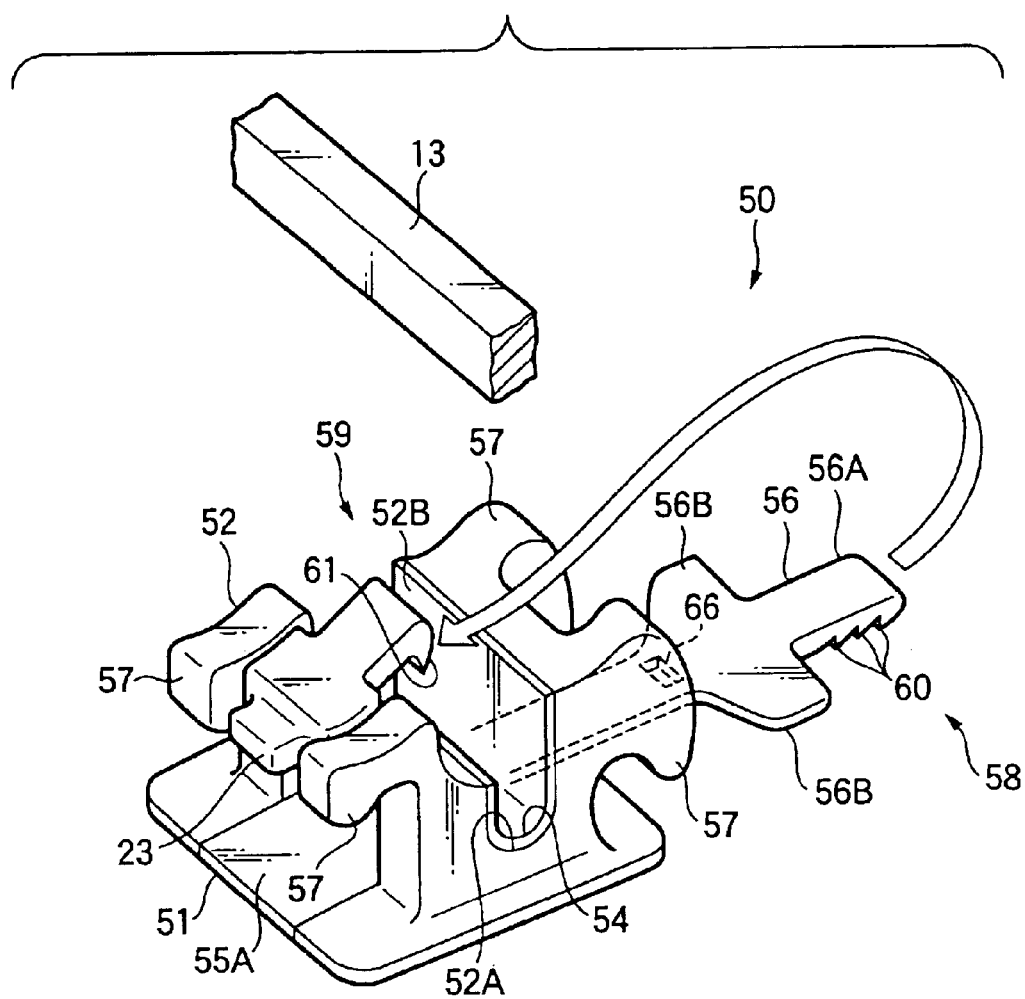
FIG. 7 is a whole perspective view showing the second embodiment according to the invention.
Figure 8:
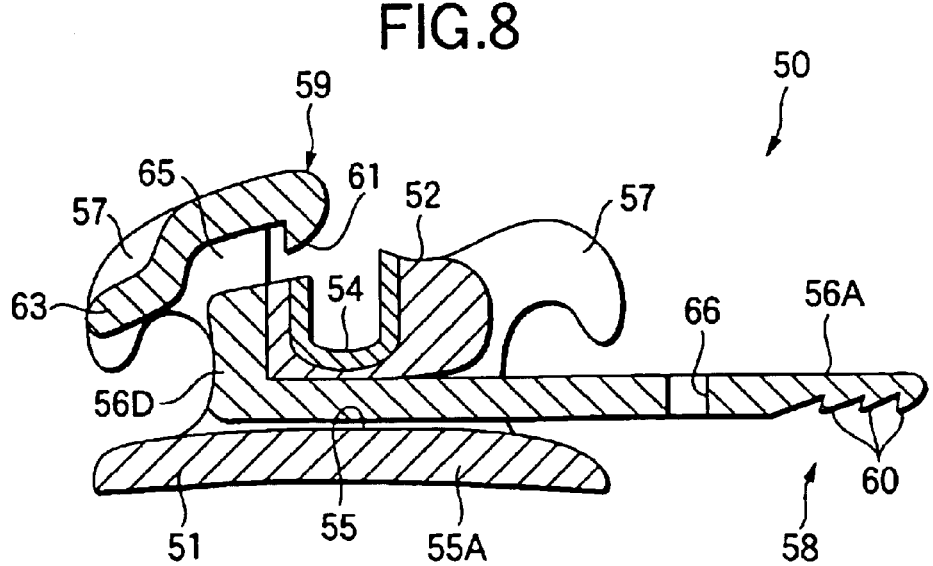
FIG. 8 is a cross sectional view showing the orthodontic bracket of the second embodiment.

As seeing in FIGS. 5 and 6, the guiding part 55 of the orthodontic bracket 50 is a groove defined in the bonding face of the base 51, and if the bonding face side of the guiding part 55 is blocked with a plate-like covering member 55A, it is a penetrating hole continuing in the direction crossing with the archwire slot 54.

The orthodontic bracket 50 has a plurality of locking claws 60 at the locking portion 58 of one end side 56A in the length direction of the clip 56, which portions 60 are shaped in plural arrangement of saw edges in cross section perpendicular to the tooth axial direction, while at the same time the cover portion 59 is integrally formed with the other end 56C in the length direction of the clip 56 through the restriction portion 56D and a pair of walls 65, 65.

Figure 9:
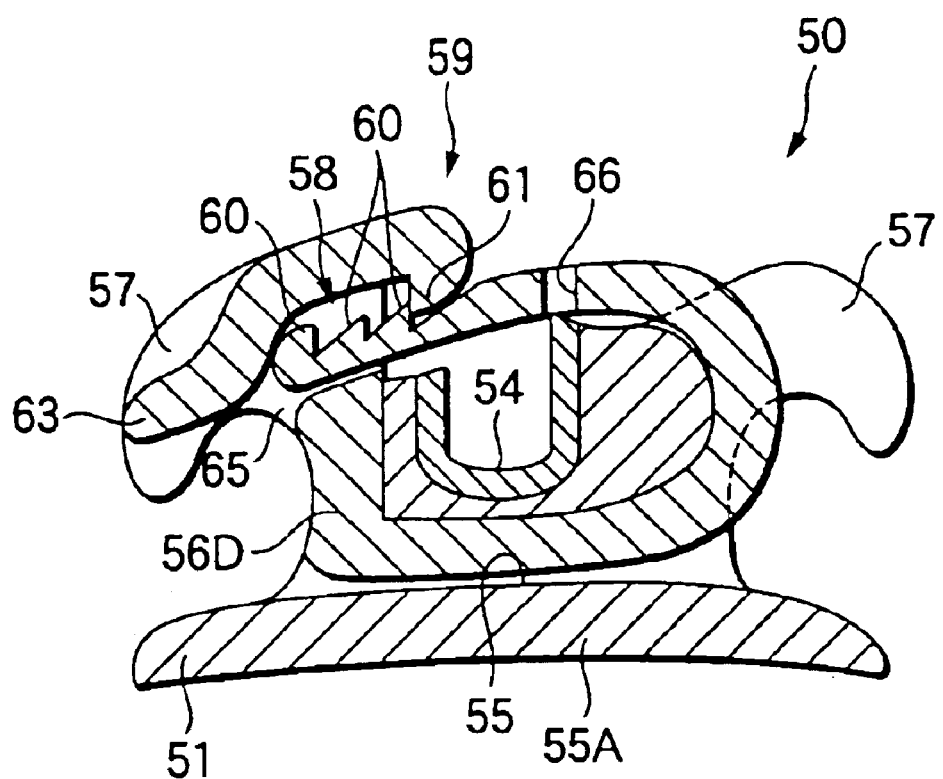
FIG. 9 is a cross sectional view showing the orthodontic bracket of the second embodiment.

The orthodontic bracket 50 receives the clip 56 in the guiding part 55 from the bonding side of the base 51, blocs the bonding side of the guiding part 55 by means of the covering member 55A and fixes it with an adhesive (see FIGS. 7 and 8), and subsequently curves the clip 56 almost in U-shape and engages the locking portion 58 as creeping under the cover portion 59, so that the locking claw 60 and the covering claw 61 elastically get over and pass each other, whereby the locking portion 58 and the cover portion 59 are engaged (see FIG. 9).

At this time, the locking claw 60 of the locking portion 58 is shaped in plural arrangement of saw edges in cross section perpendicular to the tooth axial direction, and if each of the locking claw 60 is selectively engaged with the covering claw 61, the archwire 13 can be exactly pressed toward the bottom of the archwire slot 54, irrespective of the cross sectional shapes and dimension of the archwire 13.

In the above mentioned orthodontic bracket 50, for taking out the archwire 13 from the archwire slot 54, the operator turns to deform the walls 65, 65 for releasing the mutual engagement between the locking portion 58 and the cover portion 59 in such a manner that the covering claw 61 separates from the locking claw 60 via the lever 63 extending in the direction remote from the cover portion 59.

If the operator engages the determined instrument with the drawing hole 66 formed at the determined position of the clip 56, the labial side (lip side) of the archwire slot 54 is released for taking out the archwire 13.

Depending on the orthodontic bracket 50, the locking claw 60 of the locking portion 58 and the covering claw 61 of the cover portion 59 elastically get over and pass each other, so that the locking portion 58 and the cover portion 59 are engaged, and therefore, if doing the rotational control over the certain limit, the same effect as in the first embodiment is obtained that it is possible to exactly maintain the archwire 13 positively pressing down toward the bottom of the archwire slot 54.

According to the orthodontic bracket 50, as the cover portion 59 is unified with the clip 56 in the length direction thereof, the clip 56 and the cover portion 59 may be made of soft materials having flexibility, and the bracket main body 52 may be made of hard materials.

For the orthodontic bracket 50, as the cover portion 59 is unified with the other end side 56C in the length direction of the clip 56, a plurality of kinds of bracket main bodies and clips different in specifications, dimensions and others are prepared in advance, and if associating them appropriately, variations can be easily broadened.

The locking claws 60 of the clip 56 are shaped in plural arrangement of saw edges in cross section perpendicular to the tooth axial direction, and so by appropriately selecting the relative position of the locking portion 58 with respect to the cover portion 59, the pressure of the archwire 13 can be adjusted to the archwire slot 54.

The clip 56 has a drawing hole 66 for hooking by a desired instrument, and if the operator engages the tip-end of the instrument in the drawing hole 66 after releasing the engagement of the locking portion 58 and the cover portion 59, the locking portion 58 can be easily withdrawn from the cover portion 59.

Figure 10:
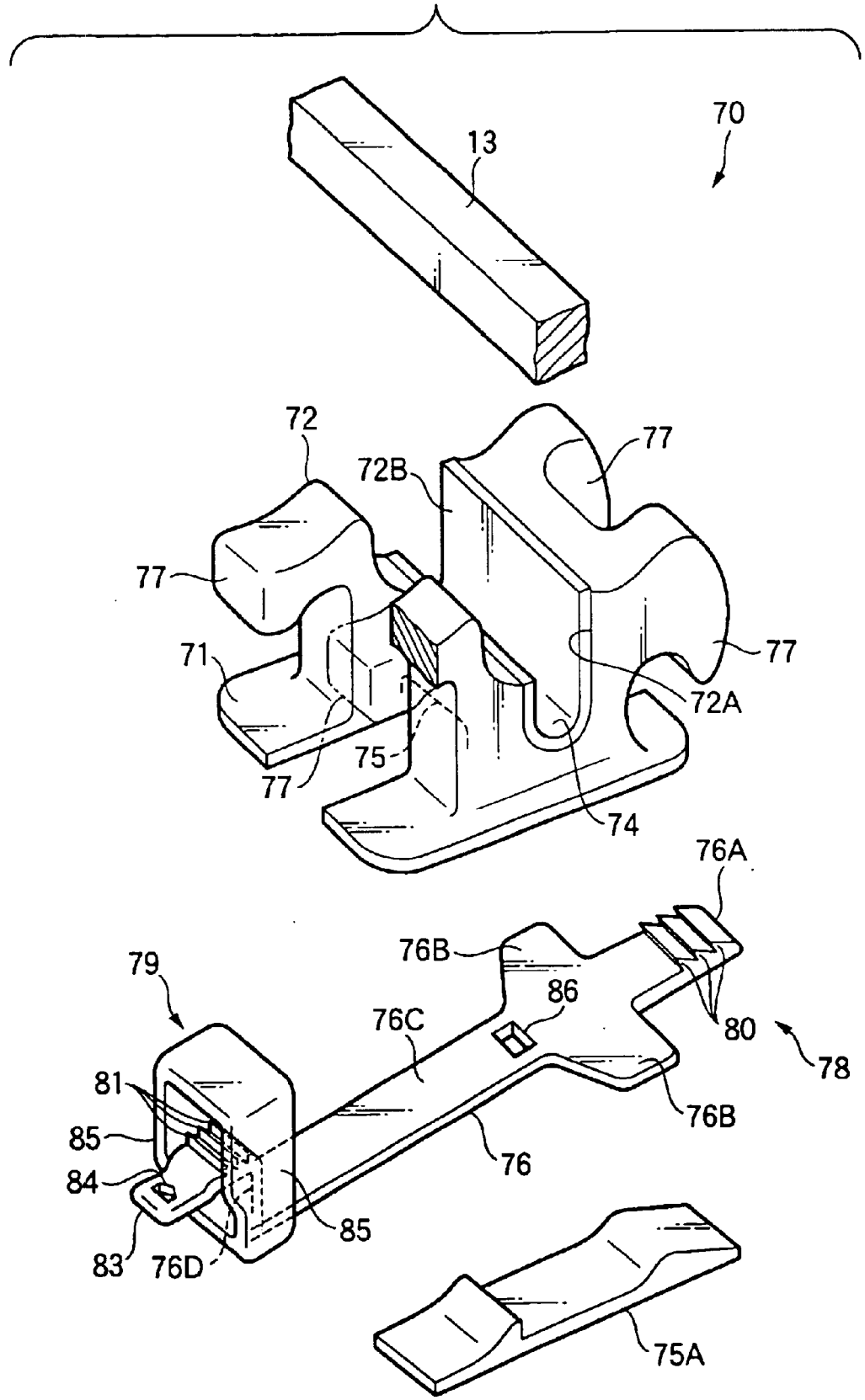
FIG. 10 is a whole perspective view showing the third embodiment according to the invention.
Figure 11:
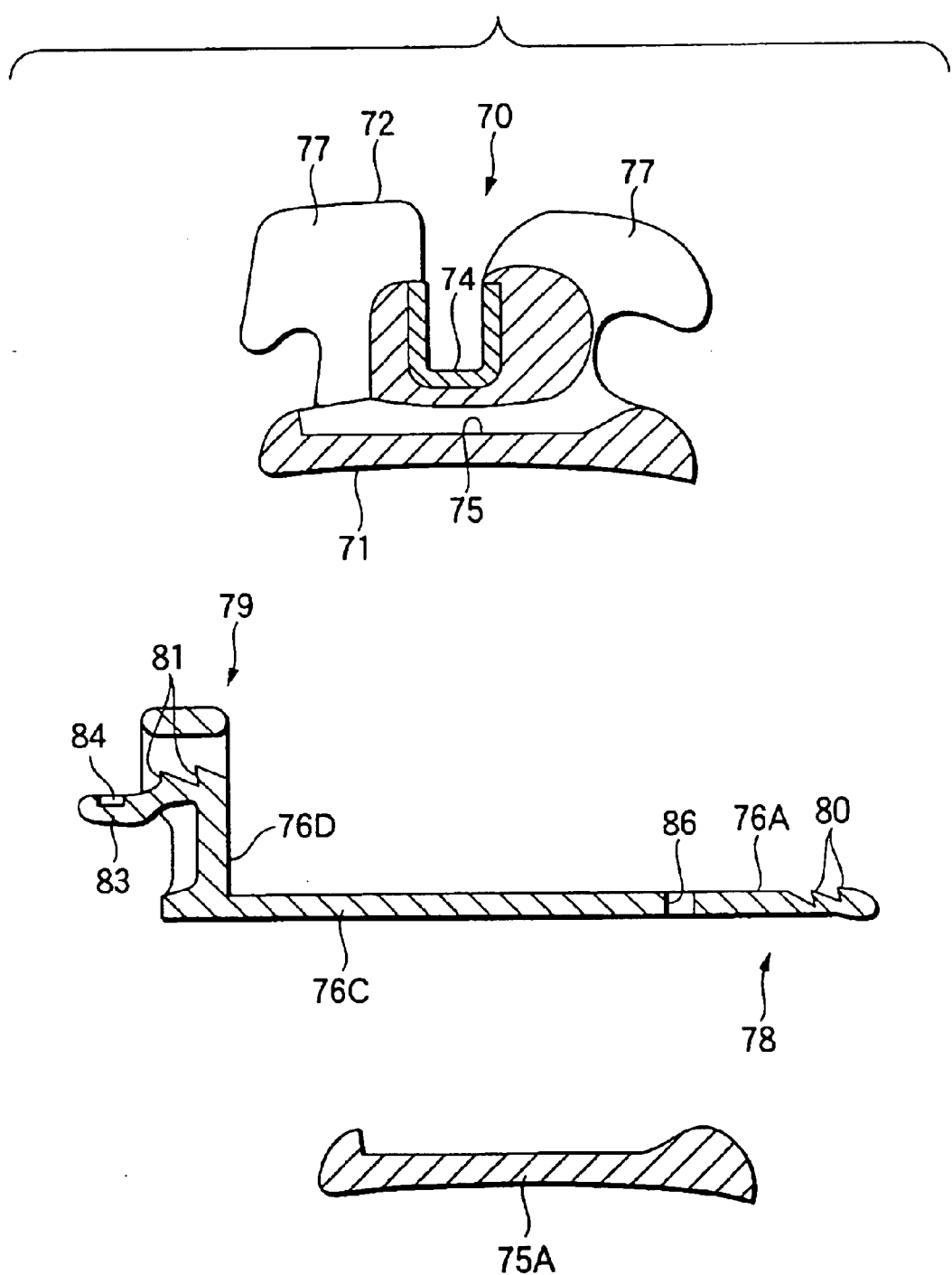
FIG. 11 is a cross sectional view showing the orthodontic bracket of the third embodiment.
Figure 12:
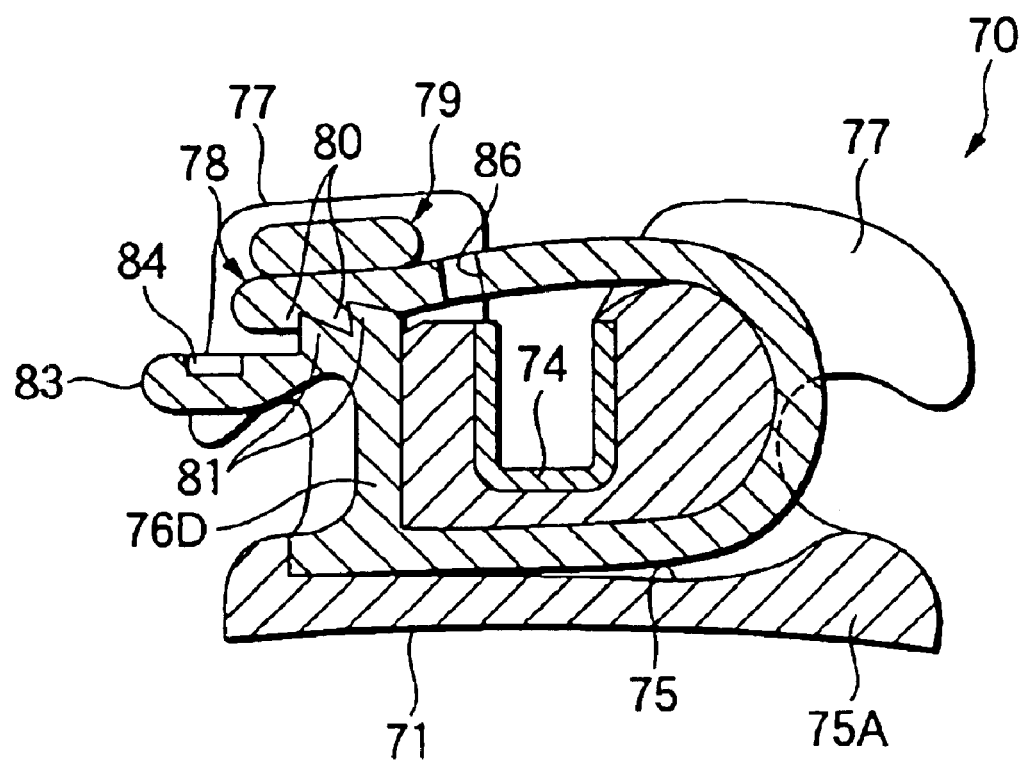
FIG. 12 is a cross sectional view showing the orthodontic bracket of the third embodiment.

FIGS. 10 to 12 show the orthodontic bracket 70 of a third embodiment according to the invention. In the third embodiment explained in the following description, the members already explained in FIGS. 1 to 9, explanation will be briefed or omitted by applying the same or corresponding signs in the drawings.

As seeing in FIGS. 10 to 12, the guiding part 75 of the orthodontic bracket 70 is a groove defined in the bonding surface of the base 71, and if the bonding surface side of the guiding part 75 is blocked with a plate-like covering portion 75A, it is a penetrating hole continuing in the direction crossing with the archwire slot 74.

The orthodontic bracket 70 has a plurality of locking claws 80 at the locking portion 78 of one end side 76A in the length direction of the clip 76, which claws 80 are shaped in plural arrangement of saw edges in cross section perpendicular to the tooth axial direction, while at the same time the cover portion 79 is integrally formed with the other end 76C in the length direction of the clip 76 through the restriction portion 76D, the cover portion 79 having the covering claw 81 which is shaped in plural arrangement of saw edges in cross section perpendicular to the tooth axial direction. With respect to the cover portion 79, the wall part 85 in almost gate shape does not contact but encircle a restriction portion 76D and the covering claws 81.

The orthodontic bracket 70 receives the clip 76 in the guiding part 75 from the bonding side of the base 71, blocks the bonding side of the guiding part 75 by means of the covering member 75A and fixes it with an adhesive (see FIG. 12), and subsequently curves the clip 76 almost in U-shape and engages the locking portion 78 as creeping under the cover portion 79, so that the locking claw 80 and the covering claw 81 elastically get over each other, whereby the locking portion 78 and the cover portion 79 are engaged.

As the orthodontic bracket 70 is basically composed as that of the second embodiment, the same effect as in the third embodiment may be obtained.

The invention is not limited to the above mentioned respective embodiments, and appropriate modifications or improvements are available.

Figure 13A:
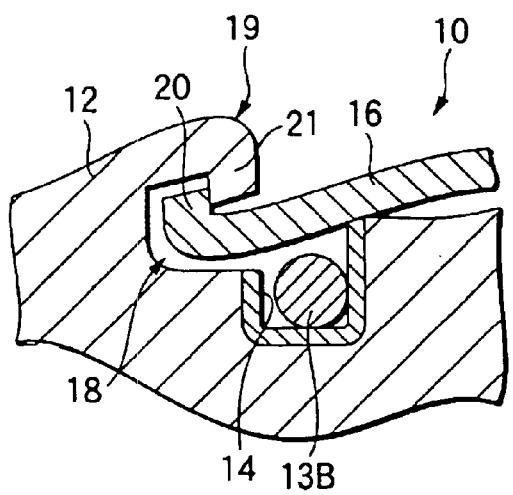
FIGS. 13A to 13D are cross sectional views of elementary parts showing modifications of the invention.
Figure 13B:
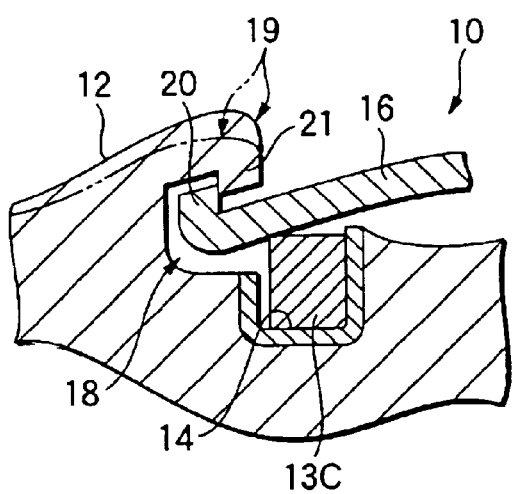

For instance, the orthodontic bracket 10 in the first embodiment can maintain the engagement of the locking claw 20 formed in the locking portion 18 and the covering claw 21 formed in the cover portion 19 even under a condition where the thin archwire 13B as shown in FIG. 13A to be used at the initial stage is received in the archwire slot 14. Further, it can also maintain the engagement of the locking claw 21 and the covering claw by turning the cover portion 19 to deform it around the fulcrum of its base under a condition where the square or rectangular archwire 13C of almost full size as shown in FIG. 13B is received in the archwire slot 14.

Figure 13C:
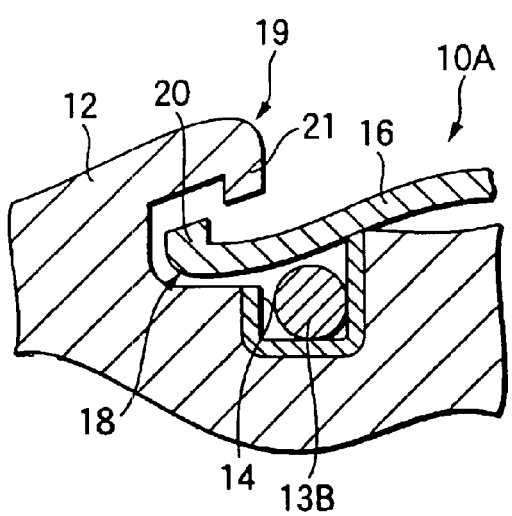

On the other hand, the orthodontic bracket 10A shown in FIG. 13C does not engage the locking claw 20 with the covering claw 21 under a condition where the archwire 13B is received in the archwire slot 14, but presses down the archwire 13B in the archwire slot 14 through elasticity of the clip 16.

Figure 13D:
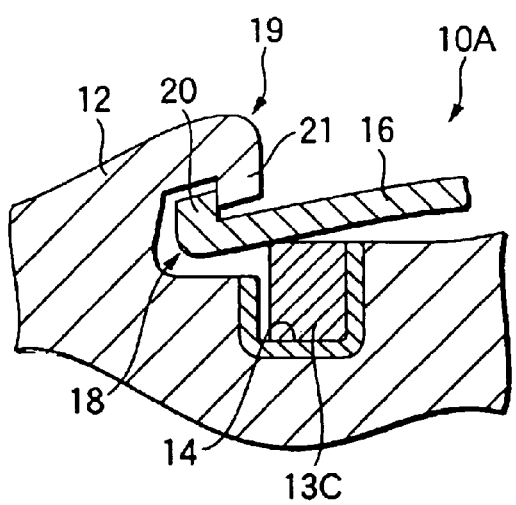
Figure 14A:
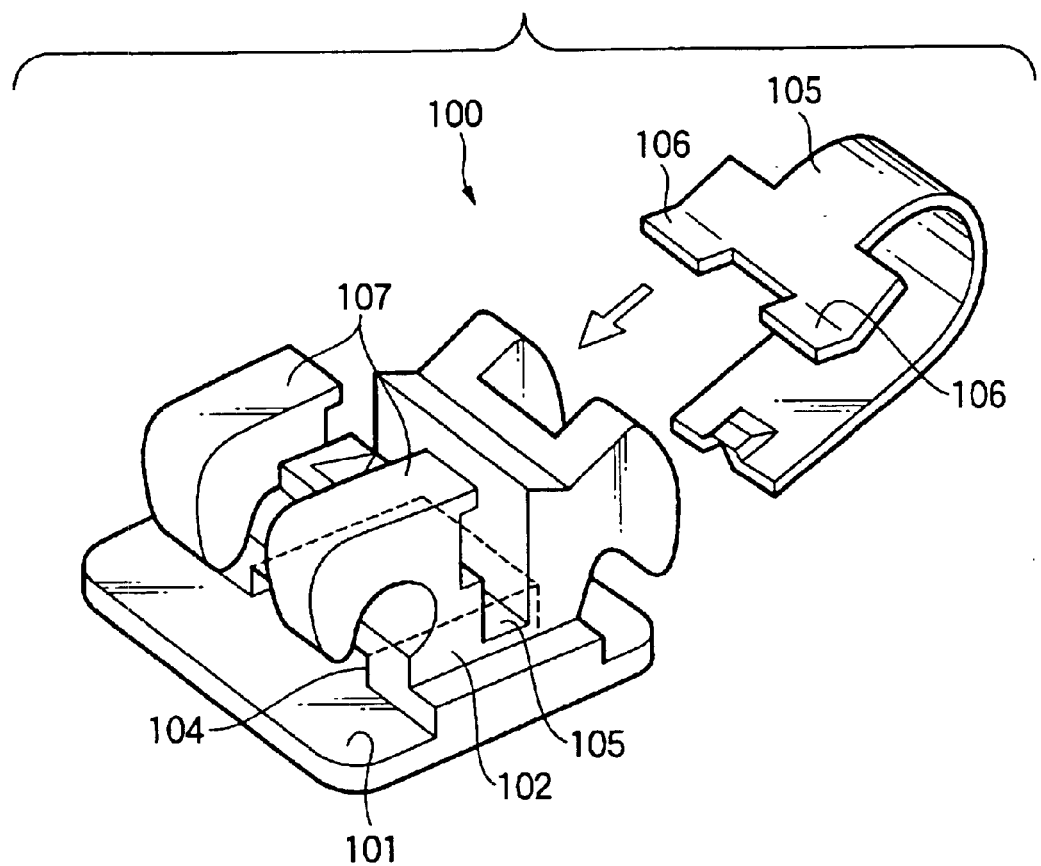
FIG. 14A is a whole perspective view and FIG. 14B is a cross sectional view showing the prior art example 1.
Figure 14B:
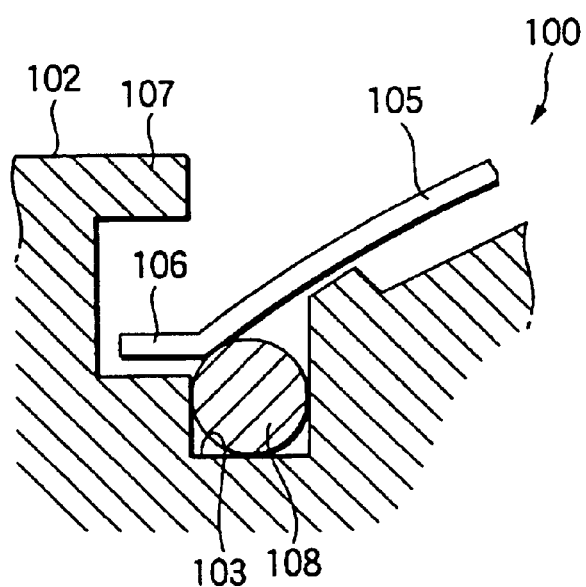
Figure 15A:
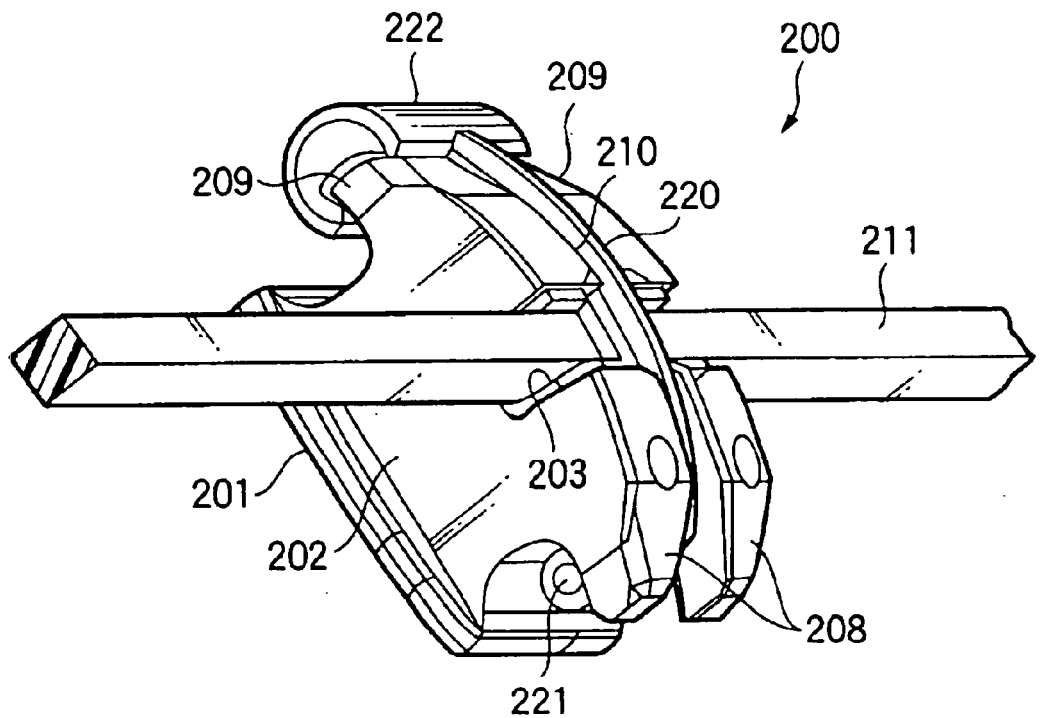
FIG. 15A and 15B is a whole perspective view and a partially perspective view showing the prior art example 2.
Figure 15B:
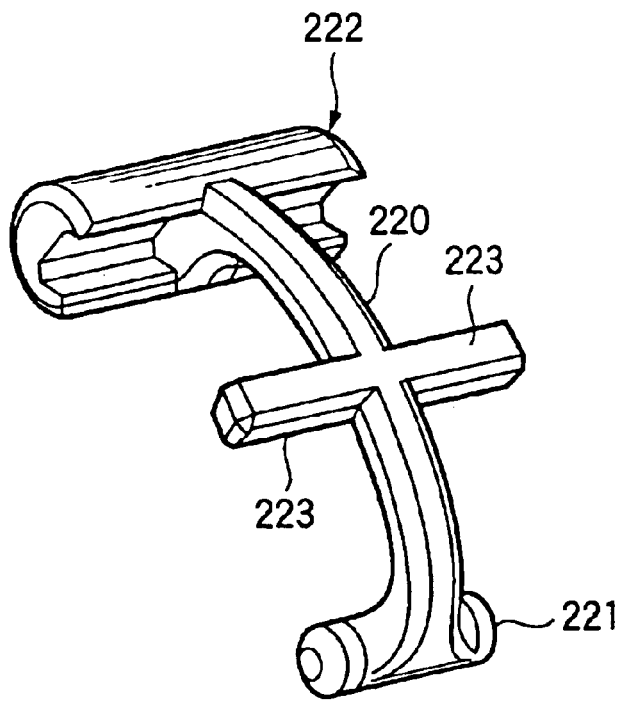

In case the orthodontic bracket 10A inserts the square or rectangular archwire 13C of almost full size in the archwire slot 14 as shown in FIG. 13D, the locking claw 20 and the covering claw 21 are engaged deeply by the archwire 13C pushing up the locking claw 20.

According to the orthodontic bracket 10A, the state of the friction free demanded at the initial stage is obtained, and at the same time, the pressure of the archwire may be maintained exactly and positively to the comparatively thick archwire used at the second and final stages.

Further, the covering claw 21 is pushed up by the locking claw 20, and the deeper the engagement, the more difficult the separation of both, so that the plastic-made clip 16 is not deviated by deformation. This invention also includes such an orthodontic bracket 10A.

With respect to the base, bracket main body, archwire slot, guiding part, clip, locking portion, cover portion, locking claw, covering claw, restriction part, lever, concave, holding part, drawing hole exemplified in each of the above mentioned embodiments, their material qualities, hues, specifications, shapes, dimensions, embodiments, number, disposing parts and others are arbitrary and limitless, as far as accomplishing the invention.

According to the present invention, it is possible to avoid a possibility that the locking portion of the clip are disengaged from the cover portion supported by the bracket main body as happening in the prior art examples depending on circumstances under the friction free state which is required to the fine archwire used at the initial stage, under the positive pressure of the comparatively thick archwire used at the second and final stages, or even when requiring the heavy rotational control for malposed teeth or rotated teeth.

As having explained above, according to the invention, the orthodontic bracket is, as set forth in the aspect (1) of the invention, that the clip is curved almost in U-shape as covering at least one part of the reverse base side in the archwire slot, and the locking portion furnished at one end side in the length direction of the clip is engaged as creeping under the cover portion supported by the bracket main body, and the orthodontic bracket has the locking claw provided at the locking portion and a covering claw provided at the cover portion, wherein the locking claw and the covering claw pass each other at a mutual locking position, so that the clip closes the archwire slot at one end side thereof in the length direction, and therefore, it is possible to avoid possibility that the locking portion of the clip gets out from the cover portion of the bracket main body as happening in the prior art examples depending on circumstances under the friction free state which is required to the thin archwire used at the curing initial stage, under the positive pressure of the comparatively thick archwire used at the second and final stages of the curing, or even when requiring the strong rotational control for malposed teeth or rotated teeth.

According to the invention, as set forth in the aspect (2), if the clip solely may press down the archwire slot at one end side in the length direction, irrespective of the locking condition between the locking claw and the covering claw, the friction free state is provided which is required to the fine archwire used at the curing initial stage, and at the same time the pressure of the archwire can be maintained securely and positively to the comparatively thick archwire used at the second and final stages of the curing.

According to the invention, as set forth in the aspect (3), if the locking claw and covering claw are disposed at positions enabling to relatively engage each other, when heavy rotational control occurs, the clip is upheaved at one end for engaging the locking claw and the covering claw, whereby if strong rotational control occurs, the locking claw and the covering claw are engaged, so that the clip can be avoided from getting out of the bracket main body.

According to the invention, as set forth in the aspect (4), if the locking claw and the covering claw elastically get over each other, thereby enabling to maintain a condition where the locking claw and the covering claw engage each other, the engagement of the locking claw and the covering claw can be securely maintained, irrespective of thickness of the archwire, so that the clip can be avoided from getting out of the bracket main body.

According to the invention, as set forth in the aspect (5), in case the locking claw and the covering claw elastically get over each other, so that the covering claw is turnable till a determined angle around a fulcrum of the base of the cover portion under the condition where the locking claw and the covering claw engage each other, even if strong rotational control is created as the covering claw is turned and deformed via the locking claw, part of force holding the archwire is received by elasticity of the cover portion, and at the same time the clip and the cover portion cooperate to press down the archwire.

According to the invention, as set forth in the aspect (6), as the cover portion is unified with the bracket main body, while a restriction part is provided at the other end side in the length direction of the clip, the force pressing down the archwire toward the bottom of the archwire slot can be borne by deforming load of the cover portion other than the clip, and also when the clip is slid by positioning the clip to release the archwire slot, the clip can be avoided from getting out of the bracket main body.

According to the invention, as set forth in the aspect (7), as the cover portion is unified with the clip in the length direction thereof, the clip and the cover portion may be made of soft materials having flexibility, and the bracket main body may be made of hard materials.

According to the invention, as set forth in the aspect (8), since the cover portion turns over a determined angle around a fulcrum of a base of the cover portion for releasing the covering claw from the locking claw, thereby enabling to release the mutual engagement of the locking portion and the cover portion, the clip is slid in a tooth-axial direction to release the archwire slot, and the archwire can be easily removed from and attached within the archwire slot, thereby enabling to lighten burden on the patient and the orthodontist.

According to the invention, as set forth in the aspect (9), as a lever is furnished in the cover portion for receiving external force turning the cover portion, if the operator pushes the lever at his fingers, nails or a tip end of an instrument, the locking portion and the cover portion can be engaged or released securely and easily.

According to the invention, as set forth in the aspect (10), as the lever is formed with a concave for receiving a determined instrument, if the operator pushes the lever at his fingers, nails or the tip end of the instrument, the locking portion and the cover portion can be engaged or released more securely and easily.

According to the invention, as set forth in the aspect (11), in the aspects (4) or (5), at least one of the locking claw and the covering claw has a slant face directing to the other, the face being shaped in taper in cross section, and the one is arranged with saw edges in cross section of one step or more perpendicular to a tooth axial direction, so that the locking claw and the covering claw get over each other easily and elastically, and, the pressure to the archwire can be adjusted in the archwire slot by appropriately selecting the relative position between the locking portion and the cover portion.

According to the invention, as set forth in the aspect (12), preferably the base and the bracket main body have light permeability, and as set forth in the aspect (13), preferably the base and the bracket main body are filler containing resins, and the filler increases durability of the base and the bracket main body and brings out a tint of white and semi-transparency.

According to the invention, as set forth in the aspect (14), the clip has the light permeability, as the aspect (15), the clip is made of resin, and as the aspect (16) more desirably the clip is a filler containing resin, and the filler increases durability of the clip and brings out a tint of white and semi-transparence.

According to the invention, as set forth in the aspect (17), the holding part is extended from the determined position of the clip in the width direction, and the clip and the holding part can press down the archwire from the whole area of the reverse base of the archwire slot, so that the rotational control of the archwire can be exactly performed.

According to the invention, as set forth in the aspect (18), the drawing hole is formed for hooking a determined instrument at a determined position in the clip under a condition where the locking portion and the cover portion are engaged each other, and therefore after the mutual engagement of the locking portion and cover portion is released, an operator hooks the tip end of the instrument into the drawing hole, thereby easily drawing out the locking portion from the cover portion.

According to the invention, as set forth in the aspect (19), the cross sectional shape of the clip is almost arc along the width direction at the place pressing down the archwire to the archwire slot while the clip is being elastically deformed so that the cross sectional shape is to be flat, and if the clip is pressed to the archwire such that the cross sectional shape is made flat, the pressure of the archwire to the archwire slot is made available due to its elastic restitution recovering to an initial shape thereof.

While there has been described in connection with the preferred embodiments of the invention, it will be obvious to those skilled in the art that various changes and modifications may be made therein without departing from the invention, and it is aimed, therefore, to cover in the appended claims all such changes and modifications as fall within the true spirit and scope of the invention.

What is claimed is:

1. An orthodontic bracket comprising:
   a base to be attached to a tooth enamel surface;
   a bracket main body formed on the base and including an archwire slot with an opening that is opened in a direction opposite to the base;
   a guiding part formed in at least one of the bracket main body and the base, said guiding part crossing the archwire slot;
   a cover portion disposed on the bracket main body and having a covering claw;
   a band-shaped clip guided by the guiding part and curved in substantially U-shape in its cross section when the clip is attached to the bracket main body, the clip having a holding part that covers at least a portion of the opening of the archwire slot, and also the clip having a locking portion that is formed at one end of the clip in its longitudinal direction, said locking portion having a locking claw,
   wherein the locking claw and the covering claw are brought in engagement with each other at a mutual locking position.

2. The orthodontic bracket as set forth in claim 1, wherein the holding part of the clip is adapted to press the archwire toward the bottom side of the archwire slot.

3. The orthodontic bracket as set forth in claim 1, wherein the locking claw and the covering claw are positioned to be engageable with each other when said archwire slot receives therein an archwire having a cross-sectional size less than a predetermined size.

4. The orthodontic bracket as set forth in claim 1, wherein the locking claw and the covering claw are slidably brought in contact with each other when the clip is assembled with the bracket main body, thereby enabling continuance of a condition where the locking claw and the covering claw engage each other.

5. The orthodontic bracket as set forth in claim 1, wherein at least one of the locking claw and the covering claw has a tapered step portion.

6. The orthodontic bracket as set forth in claim 1, wherein the holding part of the clip has a large width part as compared with a remaining part.

7. The orthodontic bracket as set forth in claim 1, wherein the locking claw and the covering claw are brought in engagement with each other at a mutual locking position, when said archwire slot receives therein an archwire having a cross-sectional size more than a predetermined size.

8. An orthodontic bracket comprising:
   a base to be attached to a tooth enamel surface;
   a bracket main body formed on the base and including an archwire slot with an opening that is opened in a direction opposite to the base;
   a guiding part formed in at least one of the bracket main body and the base, said guiding part crossing the archwire slot;
   a cover portion supported by the bracket main body and having a covering claw;
   a band-shaped clip guided by the guiding part and curved in substantially U-shape in its cross section when the clip is attached to the bracket main body, the clip having a holding part that covers at least a portion of the opening of the archwire slot, and also the clip having a locking portion that is formed at one end of the clip in its longitudinal direction, said locking portion having a locking claw,
   wherein the locking claw and the covering claw are brought in engagement with each other at a mutual locking position, and wherein the covering claw is deformable by a determined angle around a fulcrum of the cover portion in such a manner that the covering claw is slidably engaged and locked into place by the locking claw.

9. An orthodontic bracket comprising:
   a base to be attached to a tooth enamel surface;
   a bracket main body formed on the base and including an archwire slot with an opening that is opened in a direction opposite to the base;
   a guiding part formed in at least one of the bracket main body and the base, said guiding part crossing the archwire slot;
   a cover portion supported by the bracket main body and having a covering claw;
   a band-shaped clip guided by the guiding part and curved in substantially U-shape in its cross section when the clip is attached to the bracket main body, the clip having a holding part that covers at least a portion of the opening of the archwire slot, and also the clip having a locking portion that is formed at one end of the clip in its longitudinal direction, said locking portion having a locking claw,
   wherein the locking claw and the covering claw are brought in engagement with each other at a mutual locking position, and wherein the cover portion is integrally formed with the main body, and the clip has a restriction part that is formed at the other end of the clip in its longitudinal direction and positions the clip relative to the main body.

10. An orthodontic bracket comprising:
    a base to be attached to a tooth enamel surface;
    a bracket main body formed on the base and including an archwire slot with an opening that is opened in a direction opposite to the base;

a guiding part formed in at least one of the bracket main body and the base, said guiding part crossing the archwire slot;

a cover portion supported by the bracket main body and having a covering claw;

a band-shaped clip guided by the guiding part and curved in substantially U-shape in its cross section when the clip is attached to the bracket main body, the clip having a holding part that covers at least a portion of the opening of the archwire slot, and also the clip having a locking portion that is formed at one end of the clip in its longitudinal direction, said locking portion having a locking claw, wherein the locking claw and the covering claw are brought in engagement with each other at a mutual locking position, and wherein the covering claw is deformable by a determined angle around a fulcrum of the cover portion for releasing the engagement between the covering claw and the locking claw.

11. The orthodontic bracket as set forth in claim 10, wherein the cover portion comprises:

a lever for receiving external force so as to deform the covering claw.

12. The orthodontic bracket as set forth in claim 11, wherein the lever comprises a concave portion that is adapted to receive a predetermined engagement releasing instrument.

13. An orthodontic bracket comprising:

a base to be attached to a tooth enamel surface;

a bracket main body formed on the base and including an archwire slot with an opening that is opened in a direction opposite to the base;

a guiding part formed in at least one of the bracket main body and the base, said guiding part crossing the archwire slot;

a cover portion supported by the bracket main body and having a covering claw;

a band-shaped clip guided by the guiding part and curved in substantially U-shape in its cross section when the clip is attached to the bracket main body, the clip having a holding part that covers at least a portion of the opening of the archwire slot, and also the clip having a locking portion that is formed at one end of the clip in its longitudinal direction, said locking portion having a locking claw, wherein the locking claw and the covering claw are brought in engagement with each other at a mutual locking position, and wherein the clip has a drawing hole that is adapted to receive a releasing instrument for releasing an engagement between the covering claw and the locking claw.

14. The orthodontic bracket as set forth in claim 1, wherein the holding part of the clip has an arc-shaped cross sectional shape along its width direction, thereby being adapted to press down the archwire towards the bottom of the archwire slot while the clip is being elastically deformed so that the cross sectional shape is flattened.

15. An orthodontic bracket comprising:

a base to be attached to a tooth enamel surface;

a bracket main body formed on the base and including an archwire slot with an opening that is opened in a direction opposite to the base and is located in a first face, the first face being on a side of the bracket main body substantially opposite the base;

a guiding part formed in at least one of the bracket main body and the base, said guiding part having an orientation substantially perpendicular to the archwire slot;

a cover portion supported by the bracket main body, disposed substantially parallel to the first face, and including a means for engaging another member;

a clip guided by the guiding part, the clip having a holding part that covers at least a portion of the opening of the archwire slot, and also the clip having a locking portion that is formed at one end of the clip in its longitudinal direction, said locking portion having a means for locking with said means for engaging, wherein the means for locking of the clip and the means for engaging of the cover portion are brought in engagement with each other at a mutual locking position and thereby attach the clip to the bracket main body.

16. The orthodontic bracket as set forth in claim 15, wherein the cover portion is integrally formed with the clip.

17. An orthodontic bracket comprising:

a base to be attached to a tooth enamel surface;

a bracket main body formed on the base and including an archwire slot with an opening that is opened in a direction opposite to the base;

a guiding part formed in at least one of the bracket main body and the base, said guiding part crossing the archwire slot;

a cover portion supported by the bracket main body;

a band-shaped clip guided by the guiding part and having a substantially ring-shaped cross section when the clip is attached to the bracket main body, the clip having a holding part that covers at least a portion of the opening of the archwire slot, and also the clip having first and second locking portions formed at longitudinally opposing ends of the clip, said locking portions having first and second locking claws adapted to mutually engage one another to form the substantially ring-shaped cross-section of the clip, wherein the cover portion is disposed so as to bias the first and second locking claws into engagement with one another.

18. The orthodontic bracket as set forth in claim 17, wherein the cover portion is integrally formed with the clip.

* * * * *